(12) United States Patent
Chmielewski (10) Patent No.: US 6,753,455 B2
(45) Date of Patent: Jun. 22, 2004

(54) ABSORBENT CORE ATTACHMENT

(75) Inventor: Harry J. Chmielewski, Brunswick, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 09/983,993

(22) Filed: Oct. 26, 2001

(65) Prior Publication Data

US 2003/0158531 A1 Aug. 21, 2003

(51) Int. Cl.[7] ............................................. A61F 13/15
(52) U.S. Cl. ........................... 604/365; 604/385.01
(58) Field of Search ......................... 604/385.01, 358, 604/365, 385.21, 385.3

(56) References Cited

U.S. PATENT DOCUMENTS

| | | | |
|---|---|---|---|
| 5,098,423 A | 3/1992 | Pieniak et al. | |
| 5,586,979 A | 12/1996 | Thomas | |
| 5,591,155 A | 1/1997 | Nishikawa et al. | |
| 5,634,916 A | 6/1997 | Lavon et al. | |
| 5,643,242 A | 7/1997 | Lavon et al. | |
| 5,669,897 A | 9/1997 | Lavon et al. | |
| 5,693,165 A | 12/1997 | Schmitz | |
| 5,788,684 A | 8/1998 | Abuto et al. | |
| 5,941,862 A | 8/1999 | Haynes et al. | |
| 5,968,028 A | * 10/1999 | Roe et al. | 604/385.23 |
| 6,068,620 A | 5/2000 | Chmielewski | |
| 6,083,210 A | 7/2000 | Young et al. | |
| 6,113,717 A | * 9/2000 | Vogt et al. | 156/73.1 |
| 6,142,985 A | 11/2000 | Feist | |
| 6,235,011 B1 | 5/2001 | O'Connell | |
| 6,375,644 B2 | * 4/2002 | Mizutani | 604/385.01 |
| 6,436,082 B1 | * 8/2002 | Mizutani et al. | 604/385.101 |

* cited by examiner

Primary Examiner—Weilun Lo
Assistant Examiner—C. Lynne Anderson
(74) Attorney, Agent, or Firm—Hunton & Williams LLP (57) ABSTRACT

Absorbent articles having unexpectedly superior absorbency are disclosed. In particular, the absorbent articles have a roll-good type absorbent core in a novel attachment configuration that provides unexpectedly high absorbency, as well as cost efficiency.

34 Claims, 6 Drawing Sheets

PICTURE 1: Adhesive Pattern 1

FIG. 5

PICTURE 2: Adhesive Pattern 2

FIG. 6

PICTURE 3: Adhesive Pattern 3

FIG. 7

PICTURE 4: Adhesive Pattern 4

FIG. 8

ABSORBENT CORE ATTACHMENT

FIELD OF THE INVENTION

This invention relates generally to absorbent articles having unexpectedly superior absorbency. In particular, the present invention relates to absorbent articles having a roll-good type absorbent core in a novel attachment configuration that provides unexpectedly high absorbency, as well as cost efficiency.

BACKGROUND OF THE INVENTION

Disposable absorbent articles typically include a moisture-impervious backing sheet, an absorbent pad, and a liner sheet that contacts the body of a person wearing the article. Absorbent articles, such as disposable diapers, typically further comprise opposed front and rear waist portions defining a waist opening, a crotch portion disposed therebetween, and a pair of elastically contractible leg openings along the side edges of the crotch portion.

Problems with such diaper designs include shifting, shearing and conflicting movements of the article and the body of a wearer, which distort the article, and thereby cause uneven distribution of the article relative to the wearer's body and/or cause the article to move away from a position in which it is able to reliably and intimately contact the wearer's body. Such distortions cause discomfort and often result in lateral leakage of urinary or fecal material from the diaper. Further, prolonged contact of liquid or semi-solid excreta with the skin of the wearer is also aggravated under such circumstances. For example, the moisture vapor and heat generated by the bodily exudate accumulate in a pocket of the diaper, becoming trapped and then leading to conditions adjacent to a wearer's skin that promote skin irritation, infection, and the like. Although a plastic backsheet, as described above, is generally effective in precluding the passage of bodily exude outwardly, the backsheet is not efficient in preventing lateral leakage of liquids from the opposed side portions of the core sideward between the leg gathers of the backsheet and the wearer's skin. One solution to this problem, the tightening of leg gathers or leg cuffs, presents problems in terms of the comfort of the baby and further skin irritation, particularly in view of the conventional use of polymer linings on the leg cuffs.

Absorbent cores, as found in absorbent articles such as diapers, adult incontinent devices and the like, are generally attached to the absorbent article to ensure that the core stays in place. Conventionally, the absorbent core is completely attached to the topsheet and backsheet sides of the absorbent article. As a result, the cores tend to buckle and fold over on themselves in the crotch area of the article. Not only does this affect the fit and comfort of the article, but it also affects the performance because it decreases the surface area of the core that is available for fluid uptake.

Roll-good type cores that are folded or flat, and single or multiple layer roll-good cores are generally stiff and plan in the cross-direction than typical fluff/pulp cores. Accordingly, such roll-good type cores are particularly defective when completely attached to the topsheet and backsheet. Moreover, the use of complete attachment represents a waste of attachment materials and therefore results in cost inefficiency.

As is apparent from the foregoing, conventional means for attaching absorbent cores to absorbent articles are deficient in terms of effectiveness and low product quality, mechanical complexity in design, and/or associated cost inefficiencies. In view of the deficiencies of the various products and processes disclosed in the previous references, it is highly desirable to provide absorbent articles, and methods of preparing same, that are superior in absorbency and cost efficiency.

SUMMARY OF THE INVENTION

The present invention provides absorbent articles, and methods of preparing same, that are unexpectedly superior in terms of absorbency and/or cost efficiency.

An embodiment of the present invention provides an absorbent article comprising: a substantially impermeable backsheet; a permeable topsheet; an absorbent core disposed between the substantially impermeable backsheet and the permeable topsheet, said absorbent core being only partially attached to the substantially impermeable backsheet and/or the permeable topsheet.

A further embodiment of the present invention provides an absorbent article comprising: a substantially impermeable backsheet; a permeable topsheet; an absorbent core disposed between the substantially impermeable backsheet and the permeable topsheet, said absorbent core being affixed to the substantially impermeable backsheet and said permeable topsheet by a plurality of adhesive strips; wherein the plurality of adhesive strips partially cover the surface of the absorbent core.

DETAILED DESCRIPTION OF THE INVENTION

As used herein, the term "absorbent article" refers to articles that absorb and contain exudates, and more specifically refers to articles which are placed against or in proximity to the body of a wearer of the absorbent article to absorb and contain various exudates discharged from the body. A non-exhaustive list of examples of absorbent articles includes diapers, diaper cores, diaper covers, disposable diapers, training pants, feminine hygiene products and adult incontinence products. The term "disposable article" refers to absorbent articles that are intended to be discarded or partially discarded after a single use, i.e., they are not intended to be laundered or otherwise restored or reused. The term "unitary disposable absorbent article" refers to a disposable absorbent article that is essentially a single structure (i.e., it does not require separate manipulative parts such as a diaper cover and insert). As used herein, the term "diaper" refers to an absorbent article generally worn by infants and incontinent persons about the lower torso.

The claims are intended to cover all of the forgoing classes of absorbent articles, without limitation, whether disposable, unitary or otherwise. These classifications are used interchangeably throughout the specification, but are not intended to limit the claimed invention. The invention will be understood to encompass, without limitation, all classes of absorbent articles, including those described above. Preferably, the absorbent core is thin in order to improve the comfort and appearance of a garment. The employance of thin, comfortable garments is disclosed, for example without limitation in U.S. Pat. No. 5,098,423 to Pineiak et al. which is herein incorporated by reference.

The present invention provides an absorbent article having unexpectedly superior properties of absorbency, leakage protection and/or skin wellness, as well as a method of preparing and a method of using the absorbent article. In particular, the present invention is directed to an absorbent article comprising: a substantially impermeable backsheet; a permeable topsheet; an absorbent core disposed between the substantially impermeable backsheet and the skin-opposing surface of said permeable topsheet; and a low-tack adhesive disposed on the skin-facing surface of the permeable topsheet at an adhesive application zone or plurality of adhesive application zones, said adhesive application zone or plurality of adhesive application zones being selectively placed to improve the fit of the absorbent article on a wearer of said absorbent article. The present invention can be understood by the disclosure herein and/or by reference to the drawings.

The method of attaching a roll-good type core in a diaper chassis has been found to be unexpectedly significant in reducing or eliminating the amount of buckling of the diaper when on a baby. Different adhesive patterns have been looked at to minimize the effect of buckling. Lanes, or strips, of adhesive placed in discrete areas on both the topsheet-side and backsheet-side of the core can reduce the amount of buckling and force the core into a more natural form. The adhesive patterns work on both c-folded cores and non-folded cores, so are not limited to only those roll-good cores that are folded.

The present invention included several different adhesive patterns for attaching a roll-good type absorbent core. Each pattern reduces the amount of core buckling, but to varying degrees. FIGS. 1a–1f illustrates five such patterns without limitation. The patterns are illustrated as having a c-folded core, however, the present invention is not limited to only c-folded cores, but is useful for all roll-good type cores that are folded, used in a single layer sheet, or used in multiple single layer sheets.

The patterns of adhesive manipulate the movement of the absorbent core and prevent it from buckling when worn. The adhesive pattern used in the present invention, allow movement in particular directions for different areas of the absorbent core, thereby reducing or eliminating buckling.

Roll-good type absorbent cores, including DFC, RSC, and similar materials, are more stiff and planer in the cross-direction than typical fluff/pulp cores. When the roll-good type cores are completely attached to the topsheet and backsheet sides of the absorbent article they tend to buckle and fold over on themselves in the crotch area of the diaper. Not only does this affect the fit and comfort of the diaper, but it also affects the performance because it decreases the surface area of the core that is available for fluid uptake. This problem exists for roll-good type cores that are folded or flat, and for single and multiple layer roll-good type cores. The buckling can be reduced or eliminated by selectively applying lanes or strips of adhesive on the top and bottom of the absorbent core, rather than having adhesive applied over the entire surface of the absorbent core.

Referring to FIGS. 1a–1f, a series of cross-sectional views are shown. Each view illustrates an example of an implementation of the present invention. In particular, the general placement of attachment points and/or pattern of adhesive is shown in the depictions.

Figure 1A:
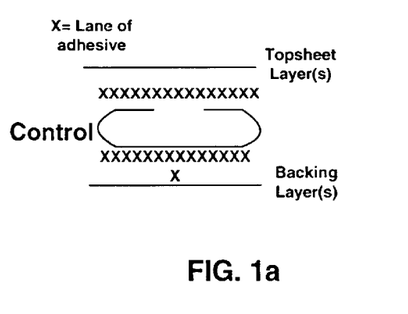
FIGS. 1a–1f are cross-sectional views of non-limiting examples of various implementations of the present invention illustrating the general placement of attachment points.
Figure 1B:
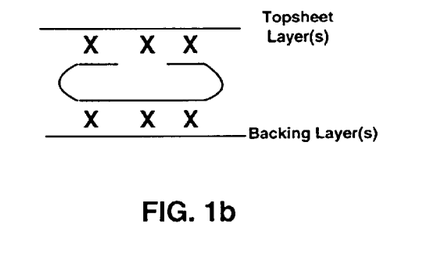
Figure 1C:
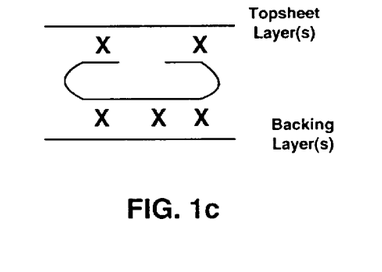
Figure 1D:
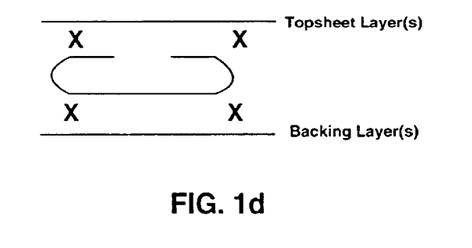
Figure 1E:
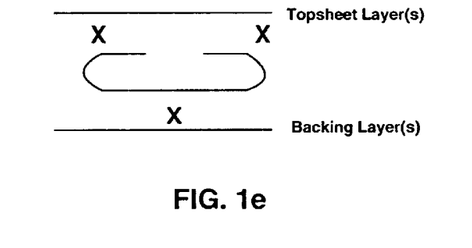
Figure 1F:
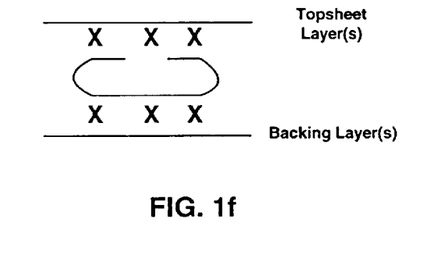
Figure 2:
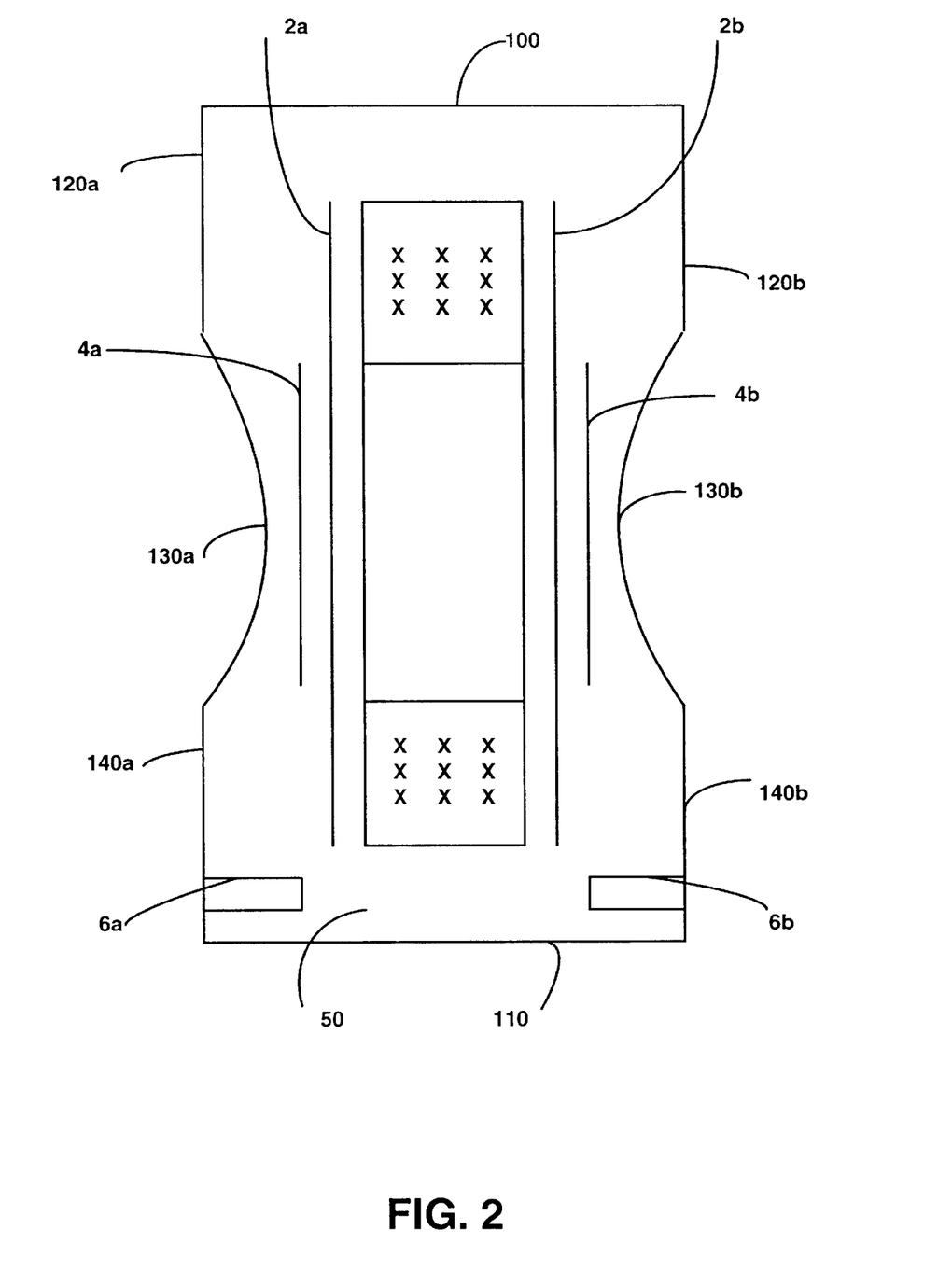
FIG. 2 is backsheet perspective view illustrating the attachment of an absorbent core to a substantially impermeable backsheet in accordance with an implementation of the present invention.

Referring to FIG. 2, a backsheet perspective view illustrating the attachment of an absorbent core to a substantially impermeable backsheet in accordance with an implementation of the present invention is shown. The absorbent article comprises a front edge 100, a back edge 110, two front-side edges 120a and 120b, two back-side edges 140a and 140b, and two leg cutout edges 130a and 130b, positioned such that leg cutout edge 130a is disposed between front-side edge 120a and back-side edge 140a, and leg cutout edge 130b is disposed between front-side edge 120b and back-side edge 140b. The absorbent article further comprises two inner leg gathers 2a and 2b, each of which extends longitudinally along the topsheet of the absorbent article from the back edge 110 to the front edge 100. The inner leg gathers 2a and 2b are approximately parallel to one another and are each positioned approximately parallel to the front-side and back-side edges 120a, 120b, 140a and 140b. Further, each inner leg gather is located adjacent to and inward of the inner most portion of the leg cutout edges 130a and 130b. A pair of front wing regions are defined as the area between each front-side edge and its adjacent inner leg gather, forward of the leg cutouts. A pair of back wing regions are defined as the area between adjacent back-side edge and its adjacent inner leg gather, rearward of the leg cutouts.

As further shown in FIG. 2, the absorbent article further comprises two leg cuffs 4a and 4b, each of which is positioned approximately adjacent and parallel to each of the inner leg gathers 2a and 2b. Each of the leg cuffs is located outward of said inner leg gathers 2a and 2b. Two fasteners 6a and 6b are each located at or near the back side edge of the absorbent article. An absorbent core 8 is shown as being disposed between the permeable topsheet 40 and a substantially impermeable backsheet 50 (not shown in FIG. 1). The absorbent core 8 is positioned longitudinally along the absorbent article. Waist foam is optionally present in the absorbent article and positioned near and adjacent to the front edge 100 and/or back edge 110, on the skin-facing surface of the permeable topsheet 40.

In accordance with an implementation of the present invention, an absorbent article is substantially evenly distributed around the body of the wearer during use. Even distribution of the absorbent article is facilitated through the novel configuration of the polymer barrier and the leg cuffs. The even distribution improves fit and comfort of the absorbent article and consequently provides unexpectedly superior leakage protection.

Figure 3:
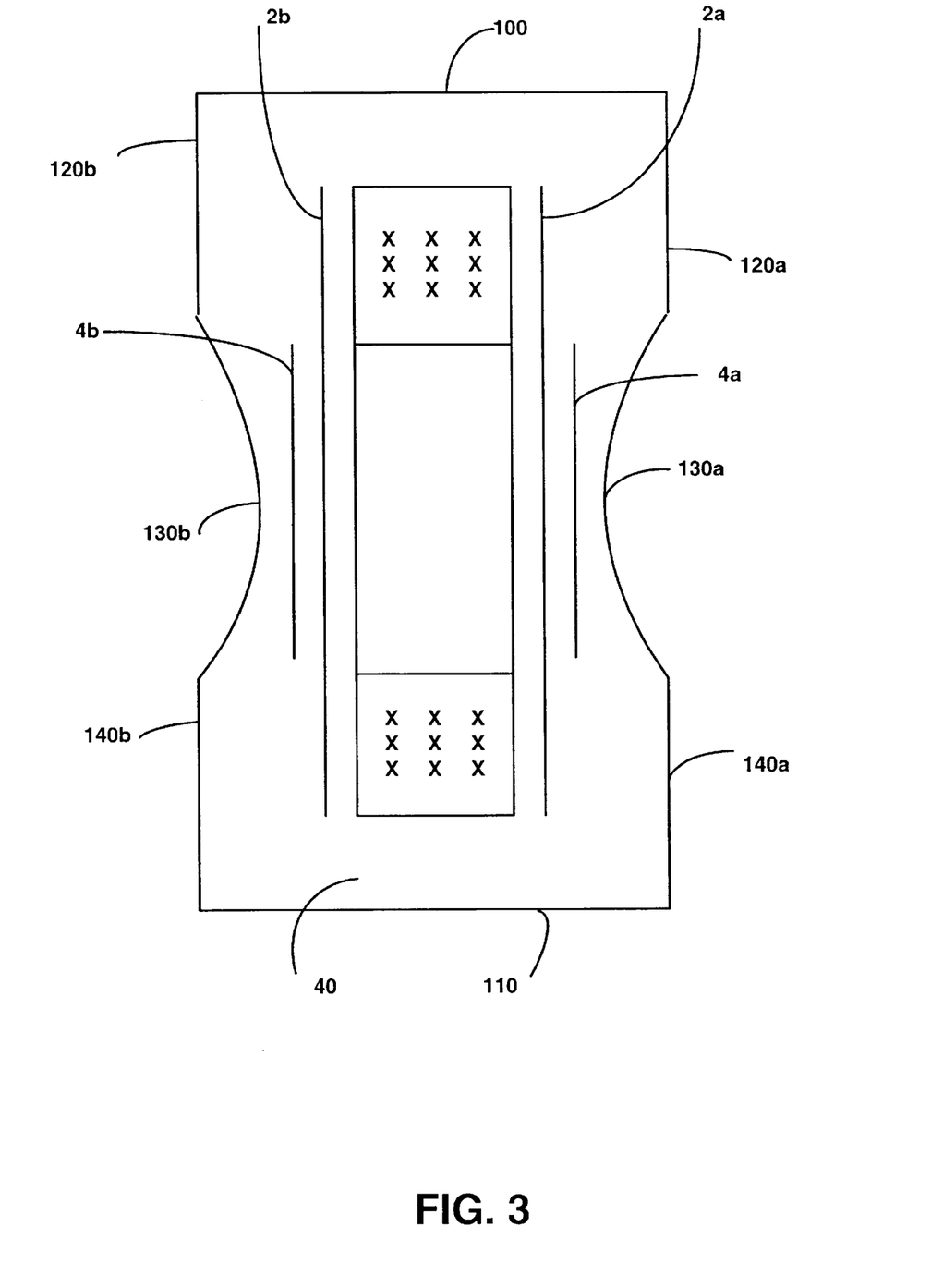
FIG. 3 is a topsheet perspective view illustrating the attachment of an absorbent core to a permeable topsheet in accordance with an implementation of the present invention.
Figure 4:
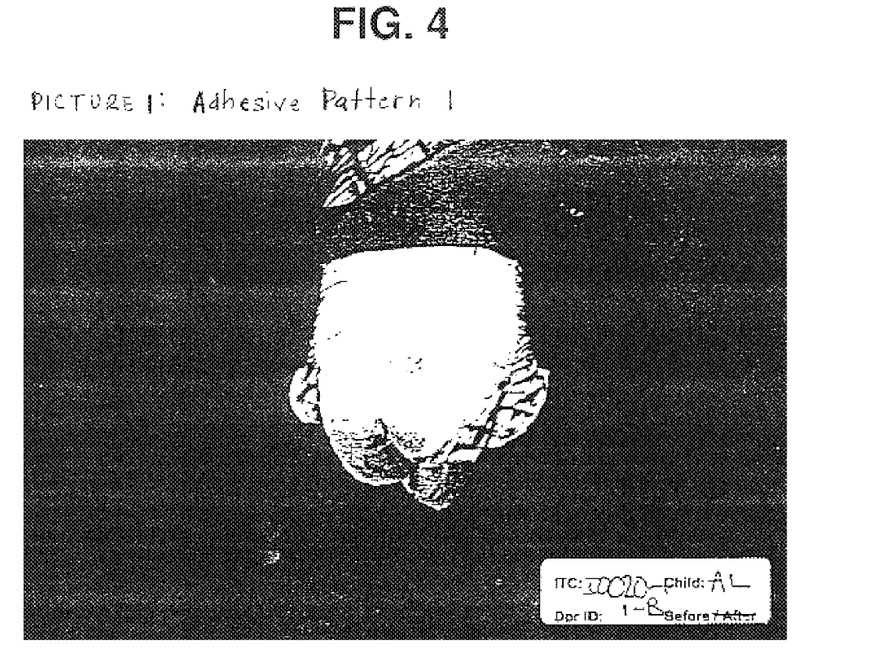
FIG. 4 is a back view of a diaper in accordance with an implementation of the present invention illustrating advantages of the adhesive pattern of FIG. 1b.
Figure 5:
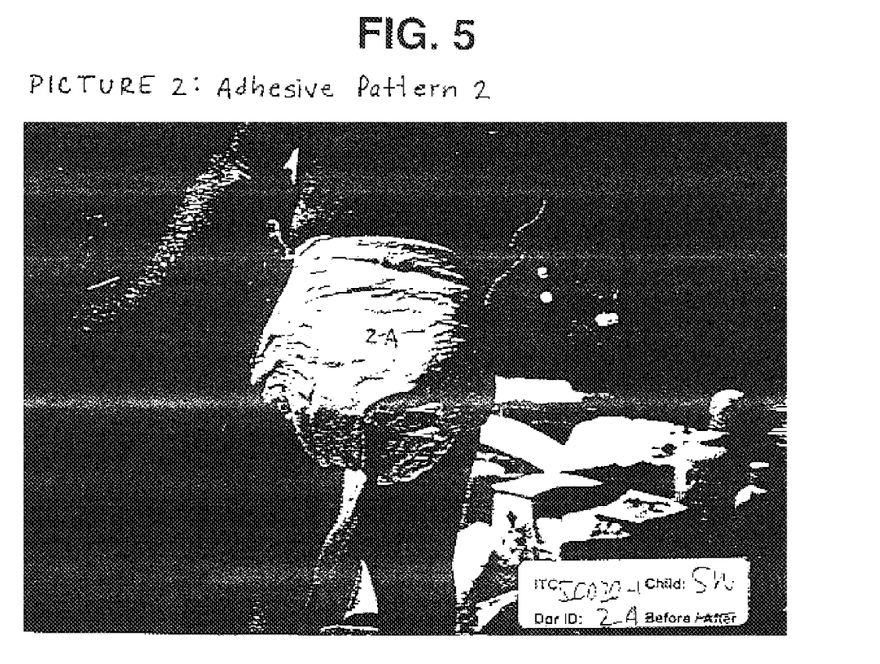
FIG. 5 is a back view of a diaper in accordance with an implementation of the present invention illustrating advantages of the adhesive pattern of FIG. 1c.
Figure 6:
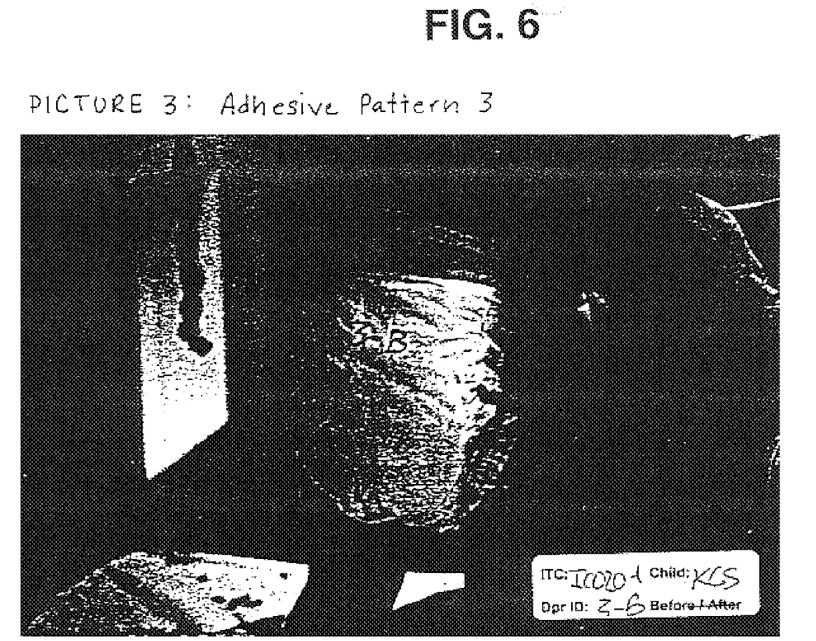
FIG. 6 is a back view of a diaper in accordance with an implementation of the present invention illustrating advantages of the adhesive pattern of FIG. 1d.
Figure 7:
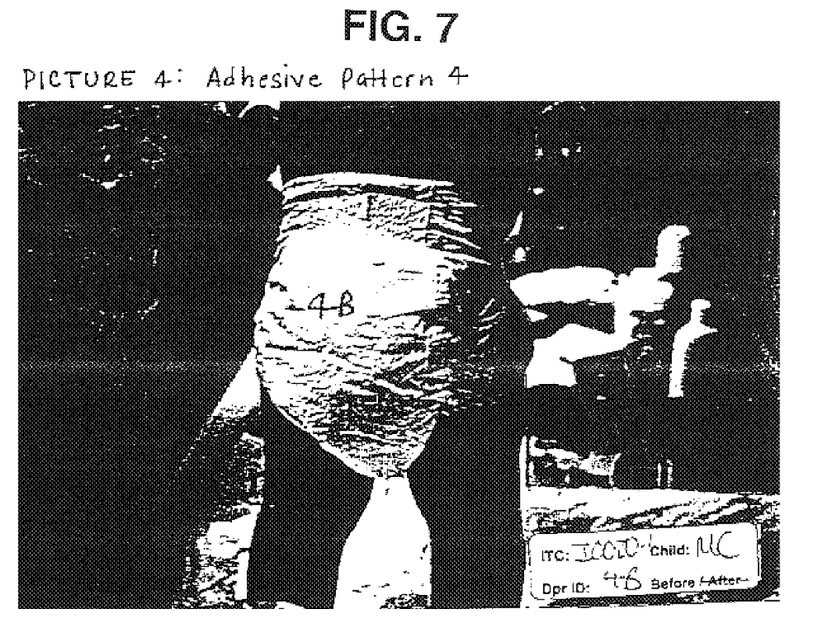
FIG. 7 is a back view of a diaper in accordance with an implementation of the present invention illustrating advantages of the adhesive pattern of FIG. 1e.
Figure 8:
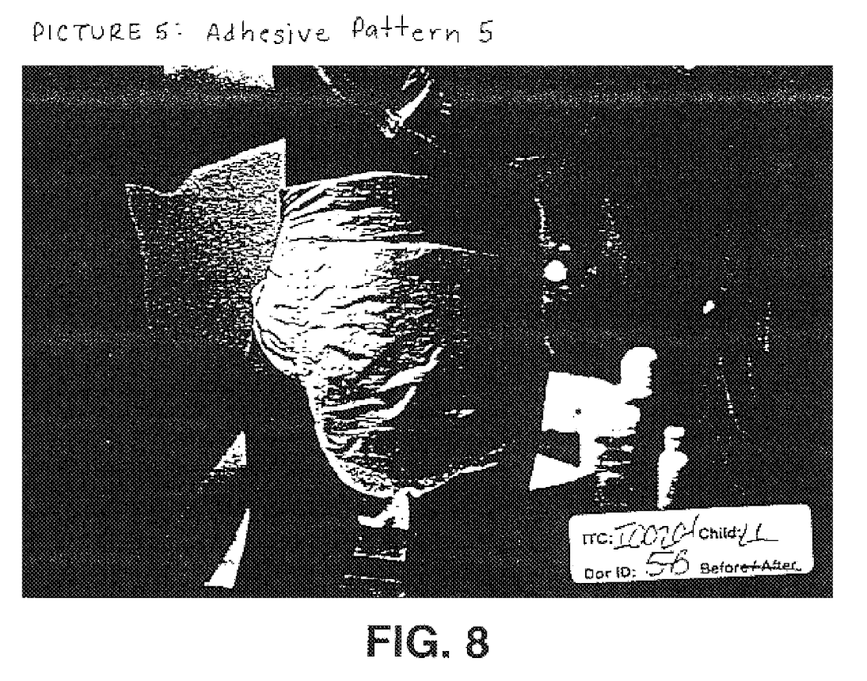
FIG. 8 is a back view of a diaper in accordance with an implementation of the present invention illustrating advantages of the adhesive pattern of FIG. 1f.

Referring to FIG. 3, a topsheet perspective view illustrating the attachment of an absorbent core to a permeable topsheet, in accordance with an implementation of the present invention, similar to that of FIG. 2, is shown.

Due to the wide variety of materials which may be incorporated into the absorbent articles of the present invention, the present invention is not intended to be limited to any specific materials. The permeable topsheet, substantially impermeable backsheet, absorbent core and other components of the absorbent articles in accordance with various implementations of the present invention may comprise various materials. Persons of ordinary skill in the art would be readily able to select appropriate materials for use in the various components of the present invention based upon the materials.

In accordance with various implementations of the present invention, the absorbent core may contain one or more fibers, one or more polymers or combinations thereof. Non-limiting exemplary fibers which may be used in the articles of the present invention include, without limitation, cellulose fibers, cellulose acetate fibers, rayon fibers, Courtauld's LYOCEL fibers, polyacrylonitrile fibers, surface modified (hydrophilic) polyester fibers, surface modified polyolophin/polyester by component fibers, surface modified polyester/polyester bicomponent fibers, cotton fibers or blends thereof. Preferably, cellulose acetate, rayon, Courtauld's LYOCEL, polyacrylonitrile, cotton fibers and cotton linters or combinations thereof are used in the present invention. More preferably, cellulose fibers are used as fiber material in the present invention.

Other materials may be added to fiber or pulp material which is optionally processed in a fiberizing apparatus, such as a hammermill. The additives may be added at any point in the process. Preferably, the additives are sprayed or injected into the airborne fibers prior to the depositing of the fibers on the forming surface 2. Non-limiting exemplary additives which may be incorporated into the process of the present invention include a polymer such as a super absorbent polymer (SAP), hydrophilic polymers, potato starch, corn starch, wheat starch or rice starch, or combinations thereof.

Various different combinations of materials may be used as are known to persons of ordinary skill in the art and which are described in U.S. Pat. No. 6,068,620 which is herein incorporated by reference. Preferably, the mixtures incorporated in the invention are substantially homogenous mixtures or uniformly distributed mixtures. Absorbent articles in accordance with an implementation of the present invention are prepared using conventional methods and materials well known to persons of ordinary skill in the art, using the guidelines provided herein.

The present invention further provides absorbent garments that include the absorbent article of the present invention. Non-limiting exemplary absorbent garments include diapers, adult incontinent products, feminine hygiene products, disposable sanitary products and the like. Non-limiting exemplary diapers include daytime diapers, nighttime diapers, daytime/nighttime diapers, long-term wear diapers, male diapers, female diapers, unisex diapers, travel diapers, medicated diapers, swimming diapers and the like.

The foregoing is considered illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

The following examples are illustrative of preferred embodiments of the invention and are not to be construed as limiting the invention thereto.

EXAMPLES

| | |
|---|---|
| Number of Participants: | Six |
| Sex of Participants | 4 Girls and 2 Boys |
| Weight Range: | 22–32 lbs. |
| Diaper/TP Size(s): | Size 4, large |

Product(s) to be Tested:

1. "A"=C fold, DFC core, No ISL (Internal spreading layer), 220 gsm SAP, 120 mm core width
2. "b"=C fold, DFC core, FX0100 airlaid ISL, 220 gsm SAP, 120 mm core width
3. "C"=Same as "B"

All three sets of the tested diapers contained varying adhesive styles, the figures herein provide illustrations of visual locations of the core adhesive, according to various embodiments of the present invention.

Product Pre-Use Observations: No defects were noted

Objective(s) and Critical Issue(s): A previous session indicated that the diapers which contained DFC cores were extremely stiff and created a large amount of inwards buckling which may have been related to the product's poor leakage results in a panel test. The following study examines the effect of varying adhesive styles on different DFC core diapers in an attempt to prevent future inward buckling.

The following Tables indicate the results of experimental studies on the various sets of diapers.

TABLE I

Diaper Change Data:
Diaper "A" = C fold, DFC core, No ISL (Internal spreading layer), 220 gsm SAP, 120 mm core width

| Child Name | Child Wt (lbs) | Waist (in) | L and R Thighs (in) | Product ID | Length of Wear (mini) | Observations |
|---|---|---|---|---|---|---|
| MC | 22 | 17 | 10, 10 | 5-A | 70 | BM; slight buttock cleavage buckling; buckling not visible at post use |
| KS | 23 | 17.5 | 11, 11 | 3-A | 70 | Slight to moderate buckling at buttock cleavage; foam folded over at 25 min.; sides winging out at 25 min.; buckling not visible at 70 min. |

TABLE I-continued

Diaper Change Data:
Diaper "A" = C fold, DFC core, No ISL (Internal spreading layer), 220 gsm SAP, 120 mm core width

| Child Name | Child Wt (lbs) | Waist (in) | L and R Thighs (in) | Product ID | Length of Wear (mini) | Observations |
|---|---|---|---|---|---|---|
| KGS | 22 | 17.5 | 9, 9.5 | 2-A | 85 | BM; slight inner buckling at buttock cleavage; buckling working its way out with wear and movement, however, when the child stood still, the buckling was visible again |
| KGS | 22 | 17.5 | 9, 9.5 | 4-A | 145 | No buckling visible; front waist gap visible at post use |
| AL | 32 | 18.2 | 10.5, 10.5 | 1-A | 85 | Buckling at buttock cleavage; buckling fell out at 65 min.; moderate fuzzing and pilling at 85 min. |
| LL | 24 | 19 | 9, 9 | 1-A | 134 | Slight inwards buckling in the crotch region; no buckling seen at 134 minutes |
| SW | 29 | 19 | 11, 11 | 2-A | 85 | Moderate buckling at buttock cleavage at 85 min.; rash on the right hip at 85 min; from the right tab |
| SW | 29 | 19 | 11, 11 | 3-A | 90 | BM; inward buckling in the crotch area; worked its way out with wear and movement |

TABLE II

Diaper "B" = C fold, DFC core, FX0100 airlaid ISL, 220 gsm SAP, 120 mm core width

| Child Name | Child Wt (lbs) | Waist (in) | L and R Thighs (in) | Product ID | Length of Wear (mini) | Observations |
|---|---|---|---|---|---|---|
| MC | 22 | 17 | 10, 10 | 1-B | 95 | Moderate to severe buttock cleavage buckling; buckling not visible at 95 min.; left buttock cheek slightly visible; loose leg fit |
| MC | 22 | 17 | 10, 10 | 2-B | 90 | Severe front inner buckling at pre-use; buckling worked it's way out with wear; foam folded over at 20 min., sides winging out at 20 min.; bottom sagging at 780 min. |
| MC | 22 | 17 | 10, 10 | 4-B | 55 | Front waist pad buckling; not visible at post use |
| KS | 23 | 17.5 | 11, 11 | 3-B | 115 | slight crotch inner buckling; worked it sway out with wear; whit chalk visible on pad prior to wear |
| AL | 32 | 18.2 | 10.5, 10.5 | 1-B | 85 | Severe inward buckling at the buttock cleavage; foam folded over at 85 min.; buckling not as severe at 85 min. |
| AL | 32 | 18.2 | 10.5, 10.5 | 4-B | 150 | Better overall fit than 1-B; no buckling seen at pre-use; slight buckling seen in the buttock cleavage at 150 min.; severe fuzzing at 150 min. |
| LL | 24 | 19 | 9, 9 | 2-B | 120 | BM; front inner crotch buckling; buckling no longer seen in the crotch region, however, buckling seen in buttock cleavage at 60 min.; both instances of buckling fell out at 120 min. |
| LL | 24 | 19 | 9, 9 | 5-B | 125 | Front crotch inner buckling seen at pre-use; buckling not visible at post-use; moderate spilling at 125 min; SAP visible around the child's genitals at 125 min. |

TABLE III

Diaper "C" = C fold, DFC core, FX0100 airlaid ISL, 220 gsm SAP, 120 mm core width

| Child Name | Child Wt (lbs) | Waist (in) | L and R Thighs (in) | Product ID | Length of Wear (mini) | Observations |
|---|---|---|---|---|---|---|
| KS | 23 | 17.5 | 11, 11 | C | 105 | Moderate to severe buckling in crotch and buttock cleavage at re-use; slight buckling at buttock cleavage at 205 min.; no buckling at the crotch visible; front waist gap at 105 min. |
| SW | 29 | 19 | 11, 11 | C | 125 | Slight buckling in buttock cleavage at pre-use; very slight buckling visible at post use |

TABLE IV

Children's Activity Level(s):
Observations: All children were considered to be VERY ACTIVE.

| | |
|---|---|
| VERY ACTIVE | Jumping, Running, Dancing, Skipping, Etc. |
| ACTIVE | Crawling, Beginning Walking; Building with Toys, Etc. |
| MODERATE | Playing with Toys Quietly, Rolling, Etc. |
| LIGHT | Reading Books, Watching Television, Etc. |
| NO ACTIVITY | Sleeping, Eating |

TABLE V

Observations: One instance of moderate redness and swelling was noted on the right hip of a child caused by the right tap of the diaper. Please not that this child has a tendency to push down on the front waist of his diapers. This continual pressure on his diaper placed the corners of the tabs into contact with his skin thus causing skin irritation.

0 Negative - No Redness or Swelling. No poke marks observed.
1 Mild Redness and/or Swelling. Poke marks observed with no visible blood.
2 Moderate Redness and/or Swelling. Poke marks observed with no visible blood.
3 Marked Redness and/or Swelling. Poke marks observed with no visible blood.
4 Intense Redness and/or Swelling. Poke marks observed with visible blood.

Leakage Observations: No instances of urine or BM leakage were noted in the session.

Fuzzing/Pilling Observations: Out of the 19 diapers worn in the session, three demonstrated instances of fuzzing and pilling. Two of the three such cases were moderate; one was 5–8 and one was 1-A. The last instance of fuzzing that was noted occurred on Diaper 4-B after 150 minutes of wear.

Pad Integrity Observations: Pad integrity observations were not performed in the session.

Parent Comments: Several parent comments were noted within the session with regard to the overall softness, aesthetics, diaper residue, and tab performance.

One parent indirectly commented on the softness of the child while talking to her child. She remarked as follows when her son had asked what she was doing: "I'm putting this soft diaper on you."

A second mother commented regarding the overall aesthetics of the TLZ as follows: "These are cute."

One parent comment was noted with regard to the tab performance of the diapers: "You're not looking at tabs are you? This one is having a hard time coming off."

Three mothers commented regarding the appearance of residue on their child at post-use. After three cases of wear, SAP was present on the child's skin. The diapers in which this occurred were as follows: 1–8,5–8. and 3–8.

ITC Summary Results and Conclusions:

18 diapers were worn in the session; 8 were Diaper "A" with varying adhesive styles, B were Diaper "A" with varying adhesive styles, and 2 were Diaper "C". Out of the 18 diapers worn in the session, 17 demonstrated instances of buckling at pre-use, however, the majority of these cases of buckling were no longer present at post-use.

Overall, it appears that Diaper "A" performed better than Diaper "B" in terms of buckling related issues. Additionally, it also appears that adhesive style number four appears to have demonstrated the least amount of buckling. For example, another adhesive style that appears to have performed as well as adhesive style number four was number five.

These variables include the following, for example:

Softness of the diaper The diapers tested in the session are noticeably softer than the previous DFC core diapers.

The varying activity levels of the children: Some children were able to work the buckling out with wear and movement quicker than some of the other children.

Total number of times each diaper variation was worn: Not every child wore one of each diaper style or variation, therefore, it is hard to pinpoint the actual reasoning behind the buckling or lack thereof. Different observations may have been noted on children with thinker/thinner legs, thinner/thinker waists, etc.

Internal Spreading Layer The presence or absence of an Internal Spreading Layer may be the reason why the diapers were not buckling as much as seen previously.

P50 Core Attachment

Number of Participants: Five
Sex of Participants: 4 Girls, 1 Boy
Weight Range: 22–32 lbs.
Diaper/TP Size(s): Size Four, Large
Product(s) to be Tested:

Diaper "A"=Ultra 3.5, Weyerhaeuser RSC 1005 Core, 120 mm core minus the c-fold, wide, single layer with no transfer layer 1. "1"=Control, pad completely attached to both the topsheet and the backsheet
2. "2"=Six points of adhesive: three across the top and three across the bottom—there are adhesive points at all corners and one at the center of the pad
3 "3"=Five paints of adhesive: two across the top and three across the bottom—for the top of the pad, the adhesive is placed at each corner. For the bottom, there is adhesive at each corner and one placement of adhesive at the center 4. "4"=Four points of adhesive: there are two points of adhesive placement for the top of the pad—both at each corner. The same is true for the bottom of the pad.
5. "5"=Three points of adhesive: Two are placed on the top of the pad with both at each corner of the pad; the last placement of adhesive is in the center of the bottom pad.

Please see diagram for visual description, however, please note that the diapers are not c-folded.

Product Pro-Use Observations: No defects noted.

Diaper Change Data:

Adhesive Version "1"=Control, pad completely attached to both the topsheet and the backsheet

TABLE VI

| Child Name | Child Wt (lbs) | Waist (in) | L and R Thighs (in) | Product ID | Length of Wear (mini) | Observations |
|---|---|---|---|---|---|---|
| GM | 22 | 16 | 9, 9 | 1 | 160 | Severe inner buckling at starting at crotch running up to just below the buttock cleavage; severe ripples of buckling still present at post use; foam folded over at 160 min. |
| LL | 24 | 19 | 9, 9 | 1 | 185 | Looks good - no buckling seen at pre-use; moderate fuzzing at 55 min.; severe fuzzing at 75 min.; urine leakage from both legs to her toes; SAP present on genitals at post-use |

TABLE VII

Adhesive Version "2" = Six points of adhesive: three across the top and three across the bottom - there are adhesive points at all corners and one at the center of the pad

| Child Name | Child Wt (lbs) | Waist (in) | L and R Thighs (in) | Product ID | Length of Wear (mini) | Observations |
|---|---|---|---|---|---|---|
| LL | 24 | 19 | 9, 9 | 2 | 30 | BM; moderate inner buckling starting at crotch up to buttock cleavage; leg gap visible on both legs at post-use; slight front waist gap; moderate skin irritation on right hop at 30 min.; slight skin irritation on left hip at 30 min. |
| AL | 32 | 18 | 11, 11 | 2 | 125 | Looks good - very slight buckling at buttock cleavage; slight fuzzing at 50 min.; moderate to severe fuzzing at 50 min.; moderate to severe fuzzing at 125 min.; spots of urine showing through the backsheet at 125 min. |

TABLE VIII

Adhesive Version "3" = Five points of adhesive: two across the top and three across the bottom - for the top of the pad, the adhesive is placed at each corner. For the bottom, there is adhesive at each corner and one placement of adhesive at the center.

| Child Name | Child Wt (lbs) | Waist (in) | L and R Thighs (in) | Product ID | Length of Wear (mini) | Observations |
|---|---|---|---|---|---|---|
| CL | 27.5 | 18 | 10, 10 | 3 | 160 | BM; severe buckling at buttock cleavage on both sides of her legs; buckling still present at 50 min., however, it appears looser; slightly runny BM leakage at both legs |
| LL | 24 | 19 | 9, 9 | 3 | 85 | Severe inner buckling at crotch up to the buttock cleavage; buckling still present 20 min. later, however, it is looser and less severe; slight front waist gap at 85 min.; foam folded over at 85 minutes. |
| AL | 32 | 18 | 11, 11 | 3 | 175 | Moderate to severe buckling by both legs; severe buckling at buttock cleavage; moderate to severe fuzzing on bottom; buckling still present but not as severe or stiff; foam folded over. |

TABLE IX

Adhesive Version "4" Four points of adhesive: there are two points of adhesive placement for the top of the pad - both at each corner. The same is true for the bottom of the pad.

| Child Name | Child Wt (lbs) | Waist (in) | L and R Thighs (in) | Product ID | Length of Wear (mini) | Observations |
|---|---|---|---|---|---|---|
| CL | 27.5 | 18 | 10, 10 | 4 | 40 | Moderate buckling at crotch at pre-use; right leg gap at post-use |
| KP | 26 | 20 | 11, 11 | 4 | 295 | Severe buckling at right leg up to buttock cleavage; buckling fee out at 70 min.; foam folded over at 295 min.; very saggy bottom at 295 min. |

TABLE X

Adhesive Version "5" Three points of adhesive: Two are placed on the top of the pad with both at each corner of the pad; the last placement of adhesive is in the center of the bottom pad.

| Child Name | Child Wt (lbs) | Waist (in) | L and R Thighs (in) | Product ID | Length of Wear (mini) | Observations |
|---|---|---|---|---|---|---|
| GM | 22 | 16 | 9, 9 | 5 | 130 | Severe buckling at crotch; bulky bottom; front waist gap at 35 min.; buckling not visible at post-use |
| CL | 27.5 | 18 | 10, 10 | 5 | 80 | Moderate buckling at left leg; left leg gap at pre-use; buckling fell out at 30 min.; moderate inner buckling at the buttock cleavage after 60 min.; buckling not visible at 80 min; slight front waist gap at 80 min.; SAP represent on child" genitals at post-use |

TABLE XI

Children's Activity Level(s):
Observations: A, C, and L were considered to be MODERATELY ACTIVE. K was considered to be ACTIVE while there where times when her activity level was LIGHT to NO ACTIVITY due to napping periods. On the other hand, G's activity level was considered to be LIGHT to MODERATE.

| | |
|---|---|
| VERY ACTIVE | Jumping, Running, Dancing, Skipping, Etc. |
| ACTIVE | Crawling, Beginning Walking; Building with Toys, Etc. |
| MODERATE | Playing with Toys Quietly, Rolling, Etc. |
| LIGHT | Reading Books, Watching Television, Etc. |
| NO ACTIVITY | Sleeping, Eating |

TABLE XII

Skin Irritation:
Observations: One instance of mild to moderate skin irritation was noted on a child wearing Diaper A", Adhesive Version 2. This instance of skin irritation was noted on both the right and left hips.

0 Negative - No Redness or Swelling. No poke marks observed.
1 Mild Redness and/or Swelling. Poke marks observed with no visible blood.
2 Moderate Redness and/or Swelling. Poke marks observed with no visible blood.
3 Marked Redness and/or Swelling. Poke marks observed with no visible blood.
4 Intense Redness and/or Swelling. Poke marks observed with visible blood.

Leakage Observations: Two instances of leakage were observed within the ITO session; one was a BM and the other was urine. The GM leakage was noted to have occurred at both legs of a child wearing Diaper "A", Adhesive Version 3. In this case the leakage that occurred took place after 160 minutes of wear and was slightly runny. The second instance of leakage that occurred was observed on both legs. This instance of leakage, which contained urine, ran all the way down to her toes after 155 minutes of wear.

Fuzzing/Pilling Observations: Three instances of moderate to severe fuzzing and pilling were noted to have occurred within the session One case of severe fuzzing and pilling was noted on the child's buttocks after 135 minutes (Diaper "A', Adhesive Version #1). The remaining two instances of moderate to severe fuzzing occurred on the same child (AL) wearing Diaper "A", Versions 2 and 3. Both children were considered to be MODERATELY ACTIVE.

Pad Integrity Observations: Pad integrity observations were not performed during the ITC session, however, one interesting visual observation was noted on Diaper "A", Adhesive Version 2. In This case Diaper "A", Adhesive Version 2 demonstrated random spots of urine visible through the backsheet. The spots were located above the buttock cleavage.

Parent Comments: Three parent comments were noted throughout the ITO session. Two of the three comments dealt with the diapers overall ability to control leakage. One mother commented as follows:

"She is really wet." The other mother commented as follows: "I like that it is thin, I just wish it could hold more." The third comment noted dealt with the overall softness of the diaper: "These are soft."

ITC Summary Results and Conclusions: 11 diapers were worn within the ITC session as follows:

Diaper "A", Version 1: 2 diapers
Diaper "A", Version 2: 2 diapers
Diaper "A", Version 3: 3 diapers
Diaper "A", Version 4: 2 diapers
Diaper "A". Version 5: 2 diapers Although there were differences at the beginning of the ITC session in terms of overall fit and buckling reduction, by the end of the session there was no clear difference in terms of fit and buckling.

Due to the increased crotch width (120 mm vs. the standard U3.5 80 mm crotch width), the diapers did not appear to fit the children very well at all. In nearly all cases of diaper wear, slight to severe buckling was visible at pre-use and/or throughout wear. Additionally, the buckling appeared to come and go depending on the child's body position and movement. What is interesting to note is that in a large majority of the cases, the buckling began near the child's legs and ran up to the buttock cleavage. In all of these cases it appeared that the increased width of the pad forced the pad to buckle upwards to accommodate for the child's small frame.

Additionally, because the pad was in fact too wide for all of the children present within the ITO session, front waist gapping was present at post-use as well. This suggests that the buckling may have forced the diaper to fit poorly not only within the crotch or buttock region, but also overall.

Related to the buckling seen on the diapers worn within the ITO session, there were three instances of inadequate leg fit. In all three cases of leg gapping seen, there was moderate to severe buckling also seen on the same side of the leg.

One may conclude that if there is inadequate leg coverage then there will also be amounts of leakage seen. In fact, there were two cases of leakage seen; one was a slightly runny BM and the other was urine. The slightly runny GM leakage occurred on both legs of a child wearing Diaper "A", Adhesive Version 3. At pre-use the same diaper demonstrated severe inner buckling at both her legs up to her buttock cleavage. The second case of leakage that occurred within the ITO session occurred on Diaper "A", Adhesive Version I and contained urine. For this diaper, the leakage that occurred was noted on both her legs and ran all the way down to her toes. This diaper demonstrated moderate inner buckling at pre-use at the crotch to the buttock cleavage. Additionally, the same diaper demonstrated left leg gapping at post-use. Please note that this diaper was worn for 185 minutes.

Overall, the diapers worn within the ITO were disastrous in terms of their inability to control or minimize inner buckling, overall fit, and absorbency. There was no diaper worn that demonstrated a dear superiority in terms of its ability to control and minimize inner buckling. With changes in movement and body position, all the diapers worn within the ITO session demonstrated buckling with some diapers demonstrating front waist.

DFC Core Attachment and U5.5 Four Strand 1W Fit Study

Number of Participants: Four
Sex of Participants: 2 Girls, 2 Boys
Weight Range: 24–31 lbs.
Diaper/TP Size(s): Size Four, Large
Product(s) to be Tested:
1. "A"=DFC Core, C-Fold, No internal Spreading Layer, 220 gsm SAP, 120 mm core width
2. "B"=DFC Core, C-Fold, FXO100 airlaid ISL, 220 gsm SAP, 120 mm core width
   Adhesive Styles
      "1"=Six points of adhesive: three across the top and three across the bottom—there are adhesive points at all corners and one at the center of the pad
      "2"=Five points of adhesive: two across the top and three across the bottom—for the top of the pad, the adhesive is placed at each corner. For the bottom, there is adhesive at each corner and one placement of adhesive at the center
      "3"=Four points of adhesive: there are two points of adhesive placement for the top of the pad—both at each corner. The same is true for the bottom of the pad.
      "4"=Three points of adhesive: there are two points of adhesive placement for the top of the pad—both at each corner. The remaining adhesive point is at the bottom, center of the pad.
3. "F=U5.5 Four Strand ILG, M1 101391512A
Product Pre-Use Observations: No defects noted.
Objective(s) and Critical Issue(s):
   RSC Core Attachment: A previous ITO session indicated that the diapers which contained DFC/RSC cores were extremely stiff and created a large amount of inwards buckling which may have been related to the product's poor leakage results within a panel test—This ITO will examine the effect of varying adhesive styles on different RSO core diapers in an attempt to prevent future inward buckling.
   U5.5 Four Strand ILG: To determine if any differences exist in the overall fit and leg fit of Diaper "F as compared to the current Ultra 5.5 diaper. Additionally, since Diaper "F' contains tour stranded 1W leg elastics, observations will be made with regards to any possible skin irritation that may result from the four stranded 1W elastics.

TABLE XIII

Diaper Change Data:
Diaper "A" = DFC Core, C-Fold, No internal Spreading Layer, 220 gain SAP, 120 mm core width

| Child Name | Child Wt (lbs) | Waist (in) | L and R Thighs (in) | Product ID | Length of Wear (mini) | Observations |
|---|---|---|---|---|---|---|
| EN1 | 31 | 22 | 12, 12 | 1-A | 30 | BM; moderate buckling at crotch; no visible at post-use when standing, however, buckling is visible when seated |

TABLE XIII-continued

Diaper Change Data:
Diaper "A" = DFC Core, C-Fold, No internal Spreading Layer, 220 gain SAP, 120 mm core width

| Child Name | Child Wt (lbs) | Waist (in) | L and R Thighs (in) | Product ID | Length of Wear (mini) | Observations |
|---|---|---|---|---|---|---|
| LL | 24 | 19 | 9, 9 | 2-A | 70 | Moderate to severe buckling at left leg; moderate fuzzing at bottom; no buckling visible at post-use; SAP present on genitals at post use; pad integrity observations performed with pad appearing completely intact with very good integrity |
| EN2 | 27 | 20 | 10, 10 | 3-A | 75 | BM; no buckling visible at pre-use; foam folded over at 75 min.; slight front waist gap |
| SW (Please note that this child has a tendency to tug on the front waist of hi diaper, therefore causing front or back waist gapping.) | 29 | 19 | 11, 11 | 4-A | 125 | BM; no buckling visible at pre-use; front/back waist gap at 125 min. |

TABLE XIV

Diaper "B" = DFC Core, C-Fold, FX0100 air-laid SAP, 120 mm core width

| Child Name | Child Wt (lbs) | Waist (in) | L and R Thighs (in) | Product ID | Length of Wear (mini) | Observations |
|---|---|---|---|---|---|---|
| EN1 | 31 | 22 | 12, 12 | 1-B | 120 | No buckling visible at pre-use; moderate fuzzing at 120 min.; SAP present on genitals at post-use; pad integrity observations performed with pad appearing completely intact with very good integrity |
| LL | 24 | 19 | 9, 9 | 2-B | 25 | BM; left buttock exposure at pre-use and post use |
| EN2 | 27 | 20 | 10, 10 | 3-B | 220 | Moderate front crotch to buttock cleavage inner buckling; moderate front waist gap at post use; no buckling present at post-use; pad integrity observations performed with pad appearing completely intact with very good integrity |
| SW (Please note that this child has a tendency to tug on the front waist of his diaper, therefore causing front or back waist gapping.) | 29 | 19 | 11, 11 | 4-B | 165 | No buckling visible; front waist gapping seen at pre-use; front waist gap at post-use |

TABLE XV

Diaper "F" U5.5 Four Strand ILG

| Child Name | Child Wt (lbs) | Waist (in) | L and R Thighs (in) | Product ID | Length of Wear (mini) | Observations |
|---|---|---|---|---|---|---|
| EN1 | 31 | 22 | 12, 12 | F-1 | 150 | Left cheek slightly exposed at pre-use and post-use; snug overall fit; slight tab stress at pre-use; moderate tab stress at post-use; no redness noted around her legs at post-use |
| LL | 24 | 19 | 9, 9 | F-1 | 155 | Good overall fit; snug leg fit visible at pre-use; slight front waist gap at post-use; no ring or irritation around either legs noted |

TABLE XVI

Children's Activity Level(s):
Observations: All children were considered to be ACTIVE; however, there was where Elijah was asleep.

| | |
|---|---|
| VERY ACTIVE | Jumping, Running, Dancing, Skipping, Etc. |
| ACTIVE | Crawling, Beginning Walking; Building with Toys, Etc. |
| MODERATE | Playing with Toys Quietly, Rolling, Etc. |
| LIGHT | Reading Books, Watching Television, Etc. |
| NO ACTIVITY | Sleeping, Eating |

TABLE XVII

Observations:
No instances of skin irritation were noted within the ITO session.

0 Negative - No Redness or Swelling. No poke marks observed.
1 Mild Redness and/or Swelling. Poke marks observed with no visible blood.
2 Moderate Redness and/or Swelling. Poke marks observed with no visible blood.
3 Marked Redness and/or Swelling. Poke marks observed with no visible blood.
4 Intense Redness and/or Swelling. Poke marks observed with visible blood.

Leakage Observations: No urine or SM leakage occurred within ITO session.

Fuzzing/Pilling Observations: Two instances of moderate fuzzing were noted within the ITO session. One instance was noted on Diaper 8-i after two hours of wear. The second case of fuzzing was noted on diaper A-2 after 70 minutes of wear. both children were considered to be ACTIVE.

Pad Integrity Observations: Four diapers were observed over the light box in an attempt to determine each diaper's pad integrity. Three of those diapers were Diaper "B', however, there were three different versions of "8": # 1, 3, and 4. The fourth diaper observed over the light box was Diaper "A", Version 2. All four diapers demonstrated very good pad integrity with all pads staying completely intact. Additionally, all voids were centered in the crotch to front waist region.

Parent Comments: Only one parent comment was noted within the ITO session regarding the waist fit of Diaper "F". This mother believed that the waist fit was too tight on her child when in fact the entire diaper appeared too tight. The mother commented as follows: 'This one seems tighter around her tummy." Interestingly, all three diapers worn by her child were the same size.

ITC Summary Results and Conclusions: 10 diapers were worn within the ITC session; 4 were Diaper "A" "(Versions 1–4). 4 were Diaper "B"" (Versions 1–4), and 2 were Diaper "F".

Each child wore Diaper "A" and Diaper "B" in the same number version, for example, Emma wore diaper's 1–6 and 1-A. This was done in order to establish a comparison between diapers and versions for overall fit and buckling related issues.

For Diapers "A" and "B", Version #1, 8–1 appeared to fit better than A-A-1 with A-A-1 demonstrating moderate buckling at the crotch which was visible on and off during wear and while seated. Pad integrity observations were performed for 8-i with its pad remaining completely intact and demonstrating very good integrity. There were no pad integrity observations performed for A-A-1 since it was a GM diaper.

For Diapers "A" and "B", Version #2, 6–2 appeared to fit slightly better than A-2 in terms of buckling related issues. Diaper 8-2 demonstrated left buttock exposure at pre and post use without any instances of buckling. On the other hand, A-2 demonstrated moderate to severe buckling at the left leg at pre-use, however, no buckling was seen at post-use. Pad integrity observations were performed for only A-2 since 6-2 was a SM diaper. Over the light box, A-2's pad demonstrated very good pad integrity with the entire pad completely intact and nearly perfect in appearance.

For Diapers "A" and "6", Version #3, A-S appeared to fit better than 8-3 in terms of buckling related issues. Diaper 6-3 demonstrated moderate front crotch to buttock cleavage inner buckling as well as front waist gapping at post-use. On the other hand, A-3 demonstrated no buckling at pre-use and at post-use. Pad integrity observations were performed for only B-S since A-S was a BM diaper. Over the light box, 6-3's pad demonstrated very good pad integrity with the entire pad completely intact and nearly perfect in appearance.

For Diapers "A" and "6", Version #4, both diapers performed similarly in that no buckling was visible on either diaper or version at pre-use or at post-use. However, on both diapers, front and/or back waist gapping was visible at post-use. Pad integrity observations were performed for only 8-4 since A-4 was a BM diaper. Over the light box, 5-4's pad demonstrated very good pad integrity with the entire pad completely intact and nearly perfect in appearance.

Overall, it appears that Version #4 appeared to demonstrate the best overall fit with no buckling seen at pre or post use. On the other hand, the remaining three versions demonstrated some form of buckling or poor fit; 2 were Diaper "A" (Versions 1, 2) and 1 was Diaper "B" (Version 3).

U5.5 Four Strand 1W Fit Study

Two diapers were worn within the ITO session. In neither of the two testers wearing U5.5, four stranded ILG diapers did any instance of GM or urine leakage occur. One diaper appeared to demonstrate a very good overall fit with the leg fit appearing snug. However, although the leg fit was snug in its appearance it did not cause any irritation around the child's legs at post-use. On the second child, the diaper appeared too tight and snug around the waist and around the waist. Additionally, the same child demonstrated left cheek exposure before and after usage and tab stress before and after wear. It appeared that the diaper was entirely too small on this child whereas previous size fours on this child demonstrated a good fit for her weight and size.

The present invention has been described in connection with the preferred embodiments. These embodiments, however, are merely for example and the invention is not restricted thereto. Any examples described herein are illustrative of preferred embodiments of the inventive subject matter and are not to be construed as limiting the inventive subject matter thereto. It will be understood by persons skilled in the art that other variations and modifications can easily be made within the scope of the invention as defined by the appended claims.

What is claimed is:

1. An absorbent article comprising:
   a substantially impermeable backsheet;
   a permeable topsheet; and
   an absorbent core disposed between the substantially impermeable backsheet and the permeable topsheet, said absorbent core being partially attached to the substantially impermeable backsheet and/or said permeable topsheet; and wherein said absorbent core is not attached to the substantially impermeable backsheet and/or said permeable topsheet at the crotch area of the absorbent article.

2. The absorbent article of claim 1, wherein the absorbent core is partially attached to the substantially impermeable backsheet and/or the permeable topsheet by a plurality of attachment points.

3. The absorbent article of claim 1, wherein the plurality of attachment points forms a predetermined pattern on the absorbent article.

4. The absorbent article of claim 1, wherein the plurality of attachment points forms a banded or striped pattern on the absorbent article.

5. The absorbent article of claim 4, wherein the banded or striped pattern comprises adhesive strips extending from about the front edge or back edge of the absorbent article to about the crotch area of the absorbent article;
   wherein the adhesive strips do not extend into said crotch area.

6. The absorbent article of claim 4, wherein the banded or striped pattern on the absorbent article comprises three adjacent parallel adhesive strips disposed between the absorbent core and the permeable topsheet or substantially impermeable backsheet.

7. The absorbent article of claim 4, wherein the banded or striped pattern on the absorbent article comprises three adjacent parallel adhesive strips disposed between the absorbent core and the permeable topsheet; and two adjacent parallel adhesive strips disposed between the absorbent core and the substantially impermeable backsheet.

8. The absorbent article of claim 4, wherein the banded or striped pattern on the absorbent article comprises two adjacent parallel adhesive strips disposed between the absorbent core and the permeable topsheet; and three adjacent parallel adhesive strips disposed between the absorbent core and the substantially impermeable backsheet.

9. The absorbent article of claim 4, wherein the banded or striped pattern on the absorbent article comprises two adjacent parallel adhesive strips disposed between the absorbent core and the permeable topsheet; and two adjacent parallel adhesive strips disposed between the absorbent core and the substantially impermeable backsheet.

10. The absorbent article of claim 4, wherein the banded or striped pattern on the absorbent article comprises at least a first and second adjacent parallel adhesive strips disposed between the absorbent core and the permeable topsheet; and at least a third adjacent adhesive strip, parallel to the at least first and second adjacent parallel adhesive strips, disposed between the absorbent core and the substantially impermeable backsheet.

11. The absorbent article of claim 4, wherein the banded or striped pattern on the absorbent article comprises at least a first and second adjacent parallel adhesive strips disposed between the absorbent core and the substantially impermeable backsheet; and a third adjacent adhesive strip, parallel to the at least first and second adjacent parallel adhesive strips, disposed between the absorbent core and the permeable topsheet.

12. The absorbent article of claim 1, wherein the absorbent core is a roll-good absorbent core.

13. The absorbent article of claim 1, wherein the absorbent core is rectangular shaped.

14. An absorbent article comprising:
    a substantially impermeable backsheet;
    a permeable topsheet; and
    an absorbent core disposed between the substantially impermeable backsheet and the permeable topsheet, said absorbent core being affixed to the substantially impermeable backsheet and/or said permeable topsheet by a plurality of adhesive strips, said absorbent core is not attached to the substantially impermeable backsheet and/or said permeable topsheet at the crotch area of the absorbent article;
    wherein the plurality of adhesive strips partially cover a surface of the absorbent core.

15. The absorbent article of claim 14, wherein the plurality of adhesive strips forms a predetermined pattern on said absorbent core.

16. The absorbent article of claim 14, wherein each adhesive strip defines an approximately rectangular area.

17. The absorbent article of claim 14, wherein each adhesive strip defines a rectangular area.

18. The absorbent article of claim 14, wherein the plurality of adhesive strips forms a banded or striped pattern on the absorbent article.

19. The absorbent article of claim 14, wherein each adhesive strip extends from about the front edge or back edge of the absorbent article to about the crotch area of the absorbent article;
    wherein each adhesive strip does not extend into said crotch area.

20. The absorbent article of claim 14, wherein the plurality of adhesive strips comprises three adjacent parallel adhesive strips disposed between the absorbent core and the permeable topsheet or substantially impermeable backsheet.

21. The absorbent article of claim 14, wherein the plurality of adhesive strips comprises three adjacent parallel adhesive strips disposed between the absorbent core and the permeable topsheet; and two adjacent parallel adhesive strips disposed between the absorbent core and the substantially impermeable backsheet.

22. The absorbent article of claim 14, wherein the plurality of adhesive strips comprises two adjacent parallel adhesive strips disposed between the absorbent core and the permeable topsheet; and three adjacent parallel adhesive strips disposed between the absorbent core and the substantially impermeable backsheet.

23. The absorbent article of claim 14, wherein the plurality of adhesive strips comprises two adjacent parallel adhesive strips disposed between the absorbent core and the permeable topsheet; and two adjacent parallel adhesive strips disposed between the absorbent core and the substantially impermeable backsheet.

24. The absorbent article of claim 14, wherein the plurality of adhesive strips comprises at least a first and second adjacent parallel adhesive strips disposed between the absorbent core and the permeable topsheet; and at least a third adjacent adhesive strip, parallel to the at least first and second adjacent parallel adhesive strips, disposed between the absorbent core and the substantially impermeable backsheet.

25. The absorbent article of claim 14, wherein the plurality of adhesive strips comprises at least a first and second adjacent parallel adhesive strips disposed between the absorbent core and the substantially impermeable backsheet; and at least a third adjacent adhesive strip, parallel to the at least first and second adjacent parallel adhesive strips, disposed between the absorbent core and the permeable topsheet.

26. An absorbent article comprising:
a substantially impermeable backsheet;
a permeable topsheet;
an absorbent core disposed between the substantially impermeable backsheet and the permeable topsheet, said absorbent core being affixed to the substantially impermeable backsheet and said permeable topsheet by a plurality of adhesive strips, said absorbent core is not attached to the substantially impermeable backsheet and/or said permeable topsheet at the crotch area of the absorbent article;
wherein the plurality of adhesive strips partially cover a surface of the absorbent core and form a banded or striped pattern; and
wherein the banded or striped pattern comprises adhesive strips extending from about the front edge or back edge of the absorbent article to about the crotch area of the absorbent article;
wherein the adhesive strips do not extend into said crotch area.

27. The absorbent article of claim 26, wherein the banded or striped pattern on the absorbent article comprises three adjacent parallel adhesive strips disposed between the absorbent core and the permeable topsheet or substantially impermeable backsheet.

28. The absorbent article of claim 26, wherein the banded or striped pattern on the absorbent article comprises three adjacent parallel adhesive strips disposed between the absorbent core and the permeable topsheet; and two adjacent parallel adhesive strips disposed between the absorbent core and the substantially impermeable backsheet.

29. The absorbent article of claim 26, wherein the banded or striped pattern on the absorbent article comprises two adjacent parallel adhesive strips disposed between the absorbent core and the permeable topsheet; and three adjacent parallel adhesive strips disposed between the absorbent core and the substantially impermeable backsheet.

30. The absorbent article of claim 26, wherein the banded or striped pattern on the absorbent article comprises two adjacent parallel adhesive strips disposed between the absorbent core and the permeable topsheet; and two adjacent parallel adhesive strips disposed between the absorbent core and the substantially impermeable backsheet.

31. The absorbent article of claim 26, wherein the banded or striped pattern on the absorbent article comprises at least a first and second adjacent parallel adhesive strips disposed between the absorbent core and the permeable topsheet; and at least a third adjacent adhesive strip, parallel to the at least first and second adjacent parallel adhesive strips, disposed between the absorbent core and the substantially impermeable backsheet.

32. The absorbent article of claim 26, wherein the banded or striped pattern on the absorbent article comprises at least a first and second adjacent parallel adhesive strips disposed between the absorbent core and the substantially impermeable backsheet; and at least a third adjacent adhesive strip, parallel to the at least first and second adjacent parallel adhesive strips, disposed between the absorbent core and the permeable topsheet.

33. An absorbent garment comprising:
a substantially impermeable backsheet and a permeable topsheet; said substantially impermeable backsheet and said permeable topsheet being defined by a front edge, a back edge approximately parallel to said front edge, a pair of opposing front-side adhesive edges and a pair of opposing back-side adhesive edges, each of said front-side and back-side adhesive edges being disposed between and approximately perpendicular to the front edge and the back edge, and a pair of opposing leg cutout edges disposed between the pair of front-side edges and the pair of back-side edges; and
an absorbent core disposed between the substantially impermeable backsheet and the skin-opposing surface of said permeable topsheet, said absorbent core being partially attached to the substantially impermeable backsheet and/or the permeable topsheet by a plurality of adhesive strips, said absorbent core is not attached to the substantially impermeable backsheet and/or said permeable topsheet at the crotch area of the absorbent article.

34. The absorbent garment of claim 33, wherein the absorbent garment is a diaper.

* * * * *